US00PP29764P2

(12) United States Plant Patent
Olesen

(10) Patent No.: US PP29,764 P2
(45) Date of Patent: Oct. 23, 2018

(54) ***ROSA* HYBRID VARIETY DENOMINATION 'POULPAR104'**

(50) Latin Name: ***Rosa* hybrid**
Varietal Denomination: Poulpar104

(71) Applicant: Mogens Nyegaard Olesen, Fredensborg (DK)

(72) Inventor: Mogens Nyegaard Olesen, Fredensborg (DK)

(73) Assignee: POULSEN ROSSER A/S, Fredensborg (DK)

( * ) Notice: Subject to any disclaimer, the term of this patent is extended or adjusted under 35 U.S.C. 154(b) by 0 days.

(21) Appl. No.: 15/731,971

(22) Filed: Sep. 5, 2017

(51) Int. Cl.
*A01H 5/02* (2018.01)

(52) U.S. Cl.
USPC ..... Plt./121

(58) Field of Classification Search
USPC ..... Plt./121
See application file for complete search history.

(56) References Cited

PUBLICATIONS

PLUTO Plant Variety Database Apr. 25, 2018. p. 1.*

* cited by examiner

*Primary Examiner* — Annette H Para

(57) ABSTRACT

A new garden rose plant of the Miniature class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar104'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar104', originated as a single seedling from the stated cross.

The new variety may be distinguished from its male pollen parent and female seed parent primarily by the following characteristics. The male pollen parent plant has near white flowers while the new variety has pink flowers. The female seed parent plant grows to a height of 45 cm while the new variety grows to a height of 30 cm.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpar104' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar104' was selected in the spring of 2012 by the inventor as a single plant from the progeny of the aforementioned hybridization.

Asexual reproduction of 'Poulpar104' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpar104' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar104'.

Specifically illustrated in FIG. 1 of the drawings are open flower above view, flower petals detached, sepals detached showing receptacle and flower parts.

Figure 1:
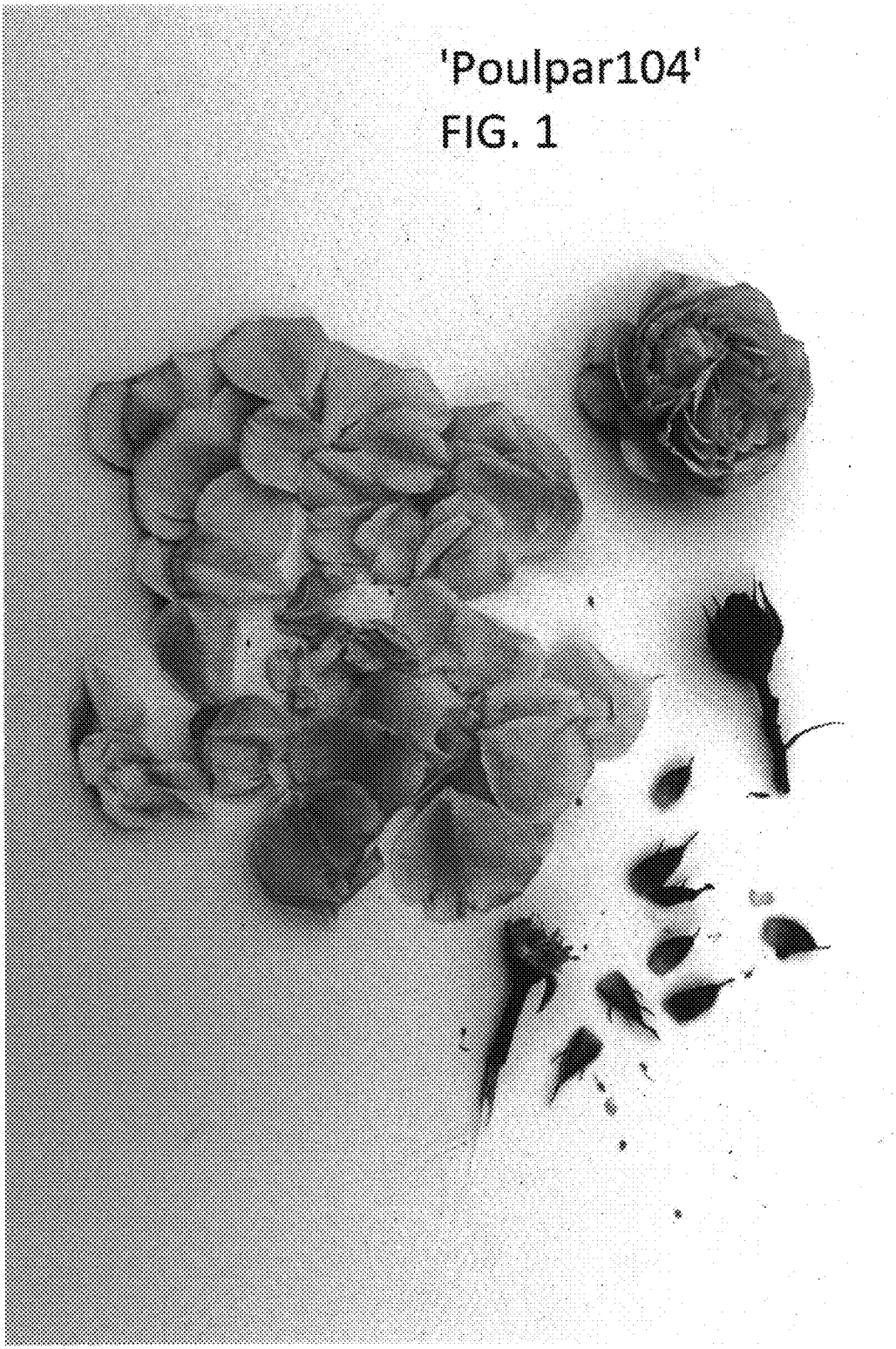
Figure 2:
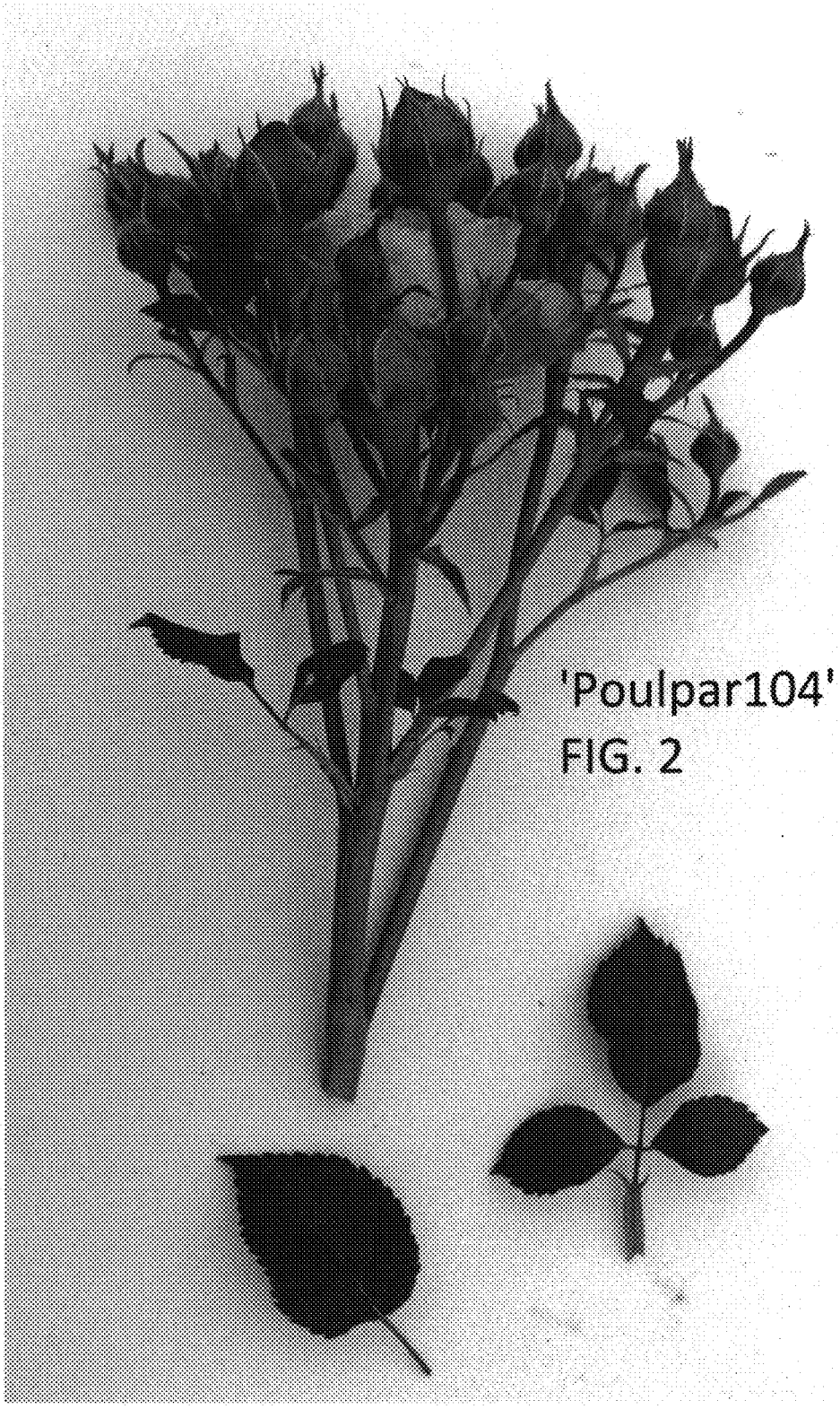

Specifically illustrated in FIG. 2 of the drawings are leaves, and a cluster of flowers on a branch. Plants shown are 2 years of age.

DETAILED DESCRIPTION OF THE VARIETY

The following is a description of 'Poulpar104', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar095', United States Plant Patent Number are compared to 'Poulpar104' in Chart 1.

CHART 1

| | 'Poulpar104' | 'Poulpar095' |
|---|---|---|
| Petal Count | 65 | 35 |
| Flower Diameter | 60 mm | 50 mm |
| General Tonality of Flower Color | blend of Red Group 49B and Red-Purple Group 62C | Red Group 55A and Red Group 38A |

FLOWER AND FLOWER BUD

Blooming habit: Continuous.

Flower bud:

*Size*.—Upon opening, 22 mm in length from base of receptacle to end of bud. Bud diameter is 17 mm.

*Bud form*.—Urceolate, nearly globose.

*Bud color*.—As sepals divide petals are Red Group 53C.

*Sepal inner surface*.—Color: Yellow-Green Group 146B with intonations of Greyed-Purple Group 183C. Surface: Lightly pubescent.

*Sepal outer surface*.—Color: Yellow-Green Group 144A with intonations of Greyed-Red Group 181B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—28 mm long, 10 mm wide.

*Receptacle*.—Texture: Smooth. Size: 5 mm in height, 9 mm wide. Color: Yellow-Green Group 144A. Shape: Funnel.

*Pedicel*.—Surface: Smooth. Length: 30 mm. Diameter: 3 mm on average. Color: Yellow-Green Group 144A. Strength: Strong.

*Peduncle*.—Length: 3 to 8 cm. Diameter: About 4 mm. Color: Yellow-Green Group N144A with light intonations of Greyed-Red Group 181B. Texture: Smooth.

Flower bud development: Flower buds are borne in clusters of about 5 flower buds on each peduncle.

Flower bloom:

*Fragrance*.—Moderate.

*Duration*.—The blooms have a duration on the plant of approximately 10 days. Petals do not fall cleanly away from plant after flowers have fully matured.

*Size*.—Flower diameter is 60 mm when open. Flower depth is 25 mm.

*Flower shape*.—Quartered-rosette, very double, with many overlapping petals packed into quarter sections.

Petalage: Under normal conditions, flowers have about 65 petals.

General tonality of flower: Open flowers are a blend of Red Group 49B and Red-Purple Group 62C.

Petal color:

*Upon and after opening, outer & inner petals*.—Upper surface: Red-Purple Group 65C with shades of White Group 155A towards basal zone. Lower surface: Blend of Red-Purple Group 69A and Red-Purple Group 68B.

*Basal petal spots*.—Upper surface: Yellow Group 4D. Lower surface: Yellow Group 4D.

Petals:

*Petal reflex*.—Not reflexed.

*Margin*.—Entire and uniform. Moderate to strong undulations.

*Shape*.—Broad and elliptic. Apex shape: Rounded. Base shape: Acute.

*Size*.—35 mm (l)×40 mm (w).

*Texture*.—Smooth.

*Thickness*.—Average.

Reproductive flower parts:

*Pollen*.—None observed.

*Anthers*.—Size: 2 mm in length. Color: Greyed-Yellow Group 162A. Quantity: 45 on average.

*Filaments*.—Color: Yellow-Orange Group 17B. Length: 4 mm.

*Pistils*.—Length: 5 mm. Quantity: 30 on average.

*Stigmas*.—Color: Greyed-Yellow Group 162A.

*Styles*.—Color: Greyed-Yellow Group 162C.

*Location of stigmas*.—Inferior in location relative to the length of the filaments and the height of the anthers.

*Hips*.—None Observed.

PLANT

Plant growth: Upright, bushy. Plants are 30 cm in height, and 25 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 6 mm.

*Internodes*.—On mature canes about 38 mm between nodes.

*Surface texture*.—Young wood: Smooth. Older wood: Smooth.

Long prickles: None observed.

Plant foliage:

*Compound leaf*.—90 mm (l)×60 mm (w).

*Quantity*.—3 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: About 22 mm long and 3 mm wide. Quantity: 2 per compound leaf. Shape: Linear, slightly broad based with outward extending apices. Margins: Finely serrated. Color: Yellow-Green Group 144A.

*Petiole*.—Length: 23 mm. Diameter: 2 mm. Upper surface color: Greyed-Red Group 179B. Lower surface color: Yellow-Green Group 144A.

*Rachis*.—Length: 28 mm. Upper surface color: Greyed-Red Group 179B. Lower surface color: Yellow-Green Group 144A.

*Leaflet*.—Quantity: Normally 5 leaflets. Margins: Serrated. Size: Terminal leaflets are 42 mm length by 30 mm wide on average. Shape: Generally elliptical. Base: Rounded. Apex: Mucronate. Texture: Smooth.

Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar104', substantially as illustrated and described herein, due to its abundant pink flowers, disease resistance, and extended period of bloom.

* * * * *

'Poulpar104'